(12) United States Patent
Bibette et al.

(10) Patent No.: US 9,277,759 B2
(45) Date of Patent: Mar. 8, 2016

(54) METHOD FOR MANUFACTURING CAPSULE SERIES, AND RELATED CAPSULE SERIES

(75) Inventors: Jérôme Bibette, Paris (FR); Liang-yin Chu, Chengdu (CN); Enric Santanach Carreras, Paris (FR); Audrey Royere, Paris (FR); Nicolas Bremond, Paris (FR)

(73) Assignee: CAPSUM, Marseilles (FR)

( * ) Notice: Subject to any disclaimer, the term of this patent is extended or adjusted under 35 U.S.C. 154(b) by 301 days.

(21) Appl. No.: 13/131,971

(22) PCT Filed: Dec. 1, 2009

(86) PCT No.: PCT/FR2009/052351
§ 371 (c)(1),
(2), (4) Date: Sep. 21, 2011

(87) PCT Pub. No.: WO2010/063937
PCT Pub. Date: Jun. 10, 2010

(65) Prior Publication Data
US 2012/0003285 A1    Jan. 5, 2012

(30) Foreign Application Priority Data
Dec. 1, 2008 (FR) ...................... 08 58172

(51) Int. Cl.
| A23L 1/22 | (2006.01) |
| A23P 1/04 | (2006.01) |
| A23L 1/00 | (2006.01) |
| A61K 9/48 | (2006.01) |

(52) U.S. Cl.
CPC ........... *A23L 1/22016* (2013.01); *A23L 1/0029* (2013.01); *A23P 1/04* (2013.01); *A61K 9/4816* (2013.01); *A61K 9/4833* (2013.01)

(58) Field of Classification Search
None
See application file for complete search history.

(56) References Cited

U.S. PATENT DOCUMENTS

| 2,799,897 | A | * | 7/1957 | Jansen | ...................... | A61J 3/07 264/241 |
| 3,423,489 | A | * | 1/1969 | Arens | ...................... | A61J 3/07 264/4 |
| 3,779,942 | A | * | 12/1973 | Bolles | ...................... | 428/402.2 |
| 3,922,360 | A | * | 11/1975 | Sneath | ...................... | 426/573 |
| 4,764,317 | A | * | 8/1988 | Anderson | ...................... | B01J 13/04 264/4 |
| 5,330,835 | A | | 7/1994 | Kikuchi et al. | | |
| 5,650,232 | A | * | 7/1997 | Glenn et al. | ...................... | 428/402.2 |
| 6,056,992 | A | | 5/2000 | Lew | | |
| 6,325,859 | B1 | * | 12/2001 | De Roos et al. | ...................... | 131/276 |
| 2004/0161498 | A1 | * | 8/2004 | Ripoll et al. | ...................... | 426/89 |
| 2004/0191366 | A1 | * | 9/2004 | Mangos et al. | ...................... | 426/89 |
| 2007/0145326 | A1 | | 6/2007 | Joseph et al. | | |

FOREIGN PATENT DOCUMENTS

| EP | 1 310 229 A1 | 5/2003 |
| GB | 2 192 171 A | 1/1988 |
| WO | 2006/136196 A1 | 12/2006 |

OTHER PUBLICATIONS

Reis, Catarina P., et al. "Review and current status of emulsion/dispersion technology using an internal gelation process for the design of alginate particles." Journal of microencapsulation 23.3 (2006): 245-257.*
International Search Report, dated May 25, 2010, from corresponding PCT application.

* cited by examiner

*Primary Examiner* — Bethany Barham
*Assistant Examiner* — Peter Anthopolos
(74) *Attorney, Agent, or Firm* — Young & Thompson

(57) ABSTRACT

A method includes separately conveying a first liquid solution (36) containing the first material and a second liquid solution (46) containing a liquid polyelectrolyte. The method includes forming of a series of drops (78) at the outlet (50), each drop (78) including a central core (80) formed from a first solution (36) and a peripheral film (82) formed from a second solution. The method includes immersing each drop (78) in a gelling solution (70) containing a reagent capable of reacting with the polyelectrolyte of the film (82) so as to form the gelled casing. The second solution (40) contains at least one surfactant before the former contacts the first solution (36).

19 Claims, 3 Drawing Sheets

METHOD FOR MANUFACTURING CAPSULE SERIES, AND RELATED CAPSULE SERIES

The present invention relates to a method for manufacturing a capsule series, each capsule comprising a liquid body containing at least one first product and a gelled casing completely encapsulating the core, the method comprising the following steps:

separately conveying, in a double casing, a first liquid solution containing the first product and a second liquid solution containing a liquid polyelectrolyte able to gel;

forming, at the outlet of the double casing, a series of drops, each drop comprising a central core formed from the first solution and a peripheral film formed from the second solution and completely covering the central core;

immersing each drop in a gelling solution containing a reagent able to react with the polyelectrolyte of the film to make it go from a liquid state to a gelled state and form the gelled casing, the central core forming the liquid core;

recovering the capsules formed.

Such capsules, which have a liquid core encapsulated by a substantially solid gelled casing, are applicable in many technical fields.

Thus, in the food industry, these capsules are used to contain various additives that make it possible to improve the properties of a food product, such as its taste or shelf life.

In the pharmaceutical or cosmetic industries, the aforementioned capsules are in particular filled with biologically or cosmetically active products. They are used in particular to protect their contents and control the salting out of the product they contain.

Such capsules are also used in biochemical applications to immobilize cells in bioreactors or as artificial cells in implants.

In all of these applications, the casings of the capsules are generally made from a material that is biocompatible with the human body. To that end, it is known to form the casing with polymers such as polysaccharides, which are biocompatible, biodegradable, and in most cases nontoxic. These polymers can advantageously go from a liquid state in solution to a noticeably more viscous state to form a gel ensuring mechanical retention of the liquid contained in the capsule.

Among these polysaccharides, alginates are in particular used to create core-casing structures in which the core is liquid.

However, the methods for making capsules with a controlled morphology (diameter, size of the casing) are tedious to carry out. Thus, the current techniques for example involve forming a solid precursor core and growing a polyelectrolyte cortex layer by layer around the core.

Once the desired cortex thickness is obtained, the solid precursor core is dissolved and the liquid product to be encapsulated is impregnated inside the cortex.

Such a technique is tedious and difficult to implement for mass production. Moreover, it is necessary to have a large quantity of products to encapsulate to impregnate the core, which is not very economical when these products are costly.

Also known from U.S. Pat. No. 6,056,992 is a method for manufacturing capsules of the aforementioned type, wherein a first solution intended to form the core and a second solution deposited around the core are co-extruded to form a drop.

The second solution contains a polymer able to thermally gel, which is put in contact with a high-temperature bath to form a gel on the surface of the capsule.

Such an approach is not fully satisfactory. Indeed, in the case where the gelling is thermally induced, it is very slow, which leads to non-homogenous casing thicknesses that are difficult to control. Furthermore, thermal gelling may not be completely reversible.

To offset this problem, it is known to use polyelectrolytes that are for example sensitive to a solution containing polyvalent ions. In this case, the reaction is fast, but it is difficult or even impossible to form drops comprising a liquid core of the first product and a liquid casing containing the polyelectrolyte for gelling without observing a separation of the phases.

It is very difficult to implement the co-extrusion method in this case, in particular for alginates.

One aim of the invention is therefore to obtain a method for manufacturing capsule series having fine casings with very controlled structures encapsulating a liquid core, this method being easy and efficient to implement.

To that end, the invention relates to a method of the aforementioned type, characterized in that the second solution contains at least one surfactant before the former contacts the first solution.

The method according to the invention can comprise one or more of the following features, considered alone or according to all technically possible combinations:

the or each surfactant is chosen among an anionic surfactant, a cationic surfactant, a non-ionic surfactant, or mixtures thereof;

the surfactant is chosen from among an alkyl sulfate, an alkyl sulfonate, an alkyl aryl sulfonate, an alkaline alkyl phosphate, a dialkyl sulfosuccinate, a salt of saturated or unsaturated alkaline earth fatty acids, a salt of alkylpyridinium or alkylammonium halide such as n-ethyldodecylammonium chloride or bromide, cetylammonium chloride or bromide, polyoxyethylenated and/or polyoxypropylenated derivatives of fatty alcohols, fatty acids, or alkylphenols, or among arylphenols, alkyl glucosides, polysorbates, cocamides, or mixtures thereof;

the total weight percentage of surfactant in the second solution is greater than 0.01% and is advantageously between 0.01% and 0.5% by mass;

the or each polyelectrolyte is a polyelectrolyte reactive to multivalent ions, in particular a polysaccharide reactive to multivalent ions such as an alginate alkaline, a gellan, or a pectin;

the ion-reactive polyelectrolyte is an alginate alkaline advantageously having an α-L-guluronate block content greater than 50%, in particular greater than 55%;

the weight percentage of polyelectrolyte in the second solution is less than 5% by mass and is advantageously between 0.5 and 3% by mass;

the ratio of the flow rate of the first solution to the flow rate of the second solution at the outlet of the double casing is between 1 and 200, advantageously between 10 and 200, the gelled casing having a thickness between 0.1% and 10%, advantageously between 0.1% and 2% of the diameter of the capsule, after recovery of the capsules formed; and the first solution comprises at least one of a biologically active product, a cosmetic product, or a comestible product suitable for consumption.

The invention also relates to capsule series, each capsule comprising a liquid core containing at least one first product, and a gelled casing completely encapsulating the liquid core at the periphery thereof, the gelled casing being able to retain the liquid core when the capsule is submerged in a gas, the gelled casing comprising at least one gelled polyelectrolyte; characterized in that the gelled casing also comprises at least one surfactant.

The invention also relates to the use of a series of capsules as defined above as a dosage unit of a cosmetic, dermatological or parapharmaceutical product.

The invention also relates to the use of capsule series as defined above as flavor beads containing a food product or sweetening pellets to be added to a beverage.

The invention also relates to the use of a capsule series as defined above as a reservoir for cell growth to perform illness detection tests or to form a bioreactor.

The invention will be better understood upon reading the following description, provided solely as an example and done in reference to the appended drawings, in which.

Figure 1:
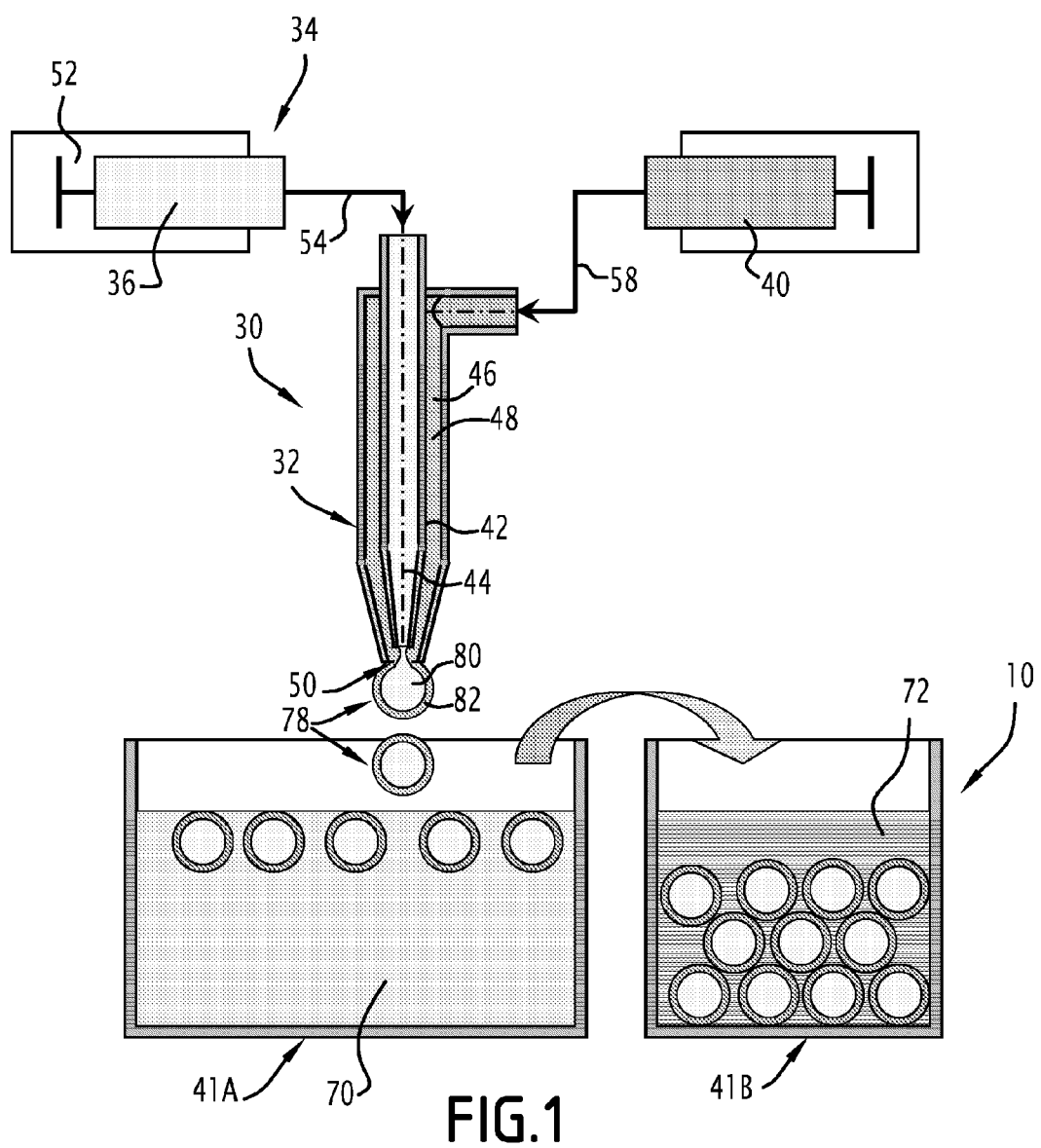
FIG. 1 is a diagrammatic cross-sectional view along a median vertical plane of a device for manufacturing capsules according to the invention, during production of a series of capsules according to the invention.
Figure 2:
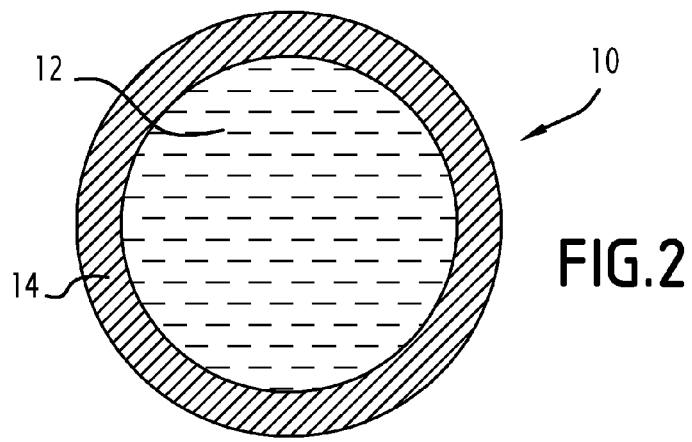
FIG. 2 is a larger-scale view, in cross-section along a median vertical plane, of a capsule according to the invention manufactured using the method shown in FIG. 1.

A first series of capsules 10 according to the invention is shown in FIG. 1. In reference to FIG. 2, each capsule 10 comprises a liquid core 12 and a gelled outer casing 14 surrounding the entire outer surface of the core 12 to retain the liquid core 12.

In this example, each capsule 10 is spherical and advantageously has an outer diameter smaller than 5 mm and in particular between 1 mm and 3 mm.

The liquid core 12 contains at least one first product advantageously chosen among a biologically active product, a cosmetic product, or a comestible product suitable for consumption.

When the first product is a biologically active product, it is advantageously chosen from among anticoagulants; anti-thrombogenics; anti-mitotic agents; anti-proliferation, anti-adhesion, anti-migration agents; cellular adhesion promoters; growth factors; anti-parasitic molecules; anti-inflammatories; angiogenics; angiogenesis inhibitors; vitamins; hormones; proteins; antifungals; antimicrobial molecules; antiseptics; or antibiotics.

Alternatively, the liquid core 12 contains reactive agents such as proteins or reagents intended to form a bioreactor, or to form artificial cells for implants.

A cosmetic product that can be contained in the core is for example cited in Directive 93/35/CEE by the Council dated Jun. 14, 1993. This product is for example a cream, an emulsion, a lotion, a gel and an oil for the skin (hands, face, feet, etc.), a foundation (liquid, paste), a bath and shower preparation (salts, foams, oils, gels, etc.), a hair care product (hair dyes and bleaches), a cleansing product (lotions, powders, shampoos), a scalp maintenance product (lotions, creams, oils), a hair styling product (lotions, lacquers, brillantines), a shaving product (soaps, foams, lotions, etc.), a product intended to be applied on the lips, a sun product, a sunless tanning product, a product for whitening the skin, an anti-wrinkle product.

Comestible products suitable for human or animal consumption are advantageously vegetable or fruit purees such as mango puree, pear puree, coconut puree, onion, leek or carrot creams, or other preparations that can mix several fruits or vegetables. Alternatively, it can involve oils such as edible oils, for example olive oil, soy oil, grape seed oil, sunflower oil, or any other oil extracted from plants.

The core 12 advantageously assumes the form of a first pure liquid product, a solution of the or each first product in a liquid solvent, a dispersion such as an emulsion or suspension of the or each first product in a liquid.

The viscosity of the liquid core 12 is less than 2000 mPa·s.

The liquid core 12 has a primarily aqueous base, or on the contrary a primarily oily phase.

The gelled casing 14 of the capsules 10 according to the invention comprises a gel containing water and at least one polyelectrolyte reactive to multivalent ions. According to the invention, the casing 14 also contains a surfactant resulting from its manufacturing method, as will be described in more detail later. "Polyelectrolyte reactive to polyvalent ions" refers, within the meaning of the present invention a polyelectrolyte able to go from a liquid state, to a gelled state under the effect of contact with a gelling solution containing multivalent ions such as ions of an alkaline earth metal chosen for example from among calcium ions, barium ions, and magnesium ions.

In the liquid state, the individual polyelectrolyte chains are substantially free to flow relative to each other. An aqueous solution with 2% by mass of polyelectrolyte then has a purely viscous behavior to the shearing gradients that are characteristic of the shaping method. The viscosity of this zero shearing solution is between 50 mPa·s and 10000 mPa·s, advantageously between 3000 mPa·s and 7000 mPa·s.

The individual chains of polyelectrolytes in liquid state advantageously have a molar mass greater than 65000 g/moles.

In the gelled state, the individual chains of polyelectrolytes form, with the multivalent ions, a coherent three-dimensional grid that retains the liquid core and prevents it from flowing. The individual chains are retained relative to each other and cannot flow freely relative to each other. In this state, the viscosity of the gel formed is infinite. Furthermore, the gel has a flow stress threshold. This stress threshold is greater than 0.05 Pa. The gel also has a non-zero modulus of elasticity greater than 35 kPa.

The three-dimensional polyelectrolyte gel contained in the casing 14 traps some the water and the surfactant. The mass content of the polyelectrolyte in the casing 12 is for example between 0.5% and 5%.

The polyelectrolyte is preferably a biocompatible polymer inoffensive to the human body. It is for example produced biologically.

Advantageously, it is chosen from among polysaccharides, acrylate-based synthetic polyelectrolytes (sodium, lithium, potassium, or ammonium polyacrylate, or polyacrylamide), sulfonate-based synthetic polyelectrolytes (sodium polystyrene sulfonate, for example). More particularly, the polyelectrolyte is chosen from among an alkaline earth alginate, such as a sodium alginate or a potassium alginate, a gellan or a pectin.

The alginates are produced from brown algae called "laminars," also referred to as "seaweed."

Such alginates advantageously have an α-L-guluronate content level greater than about 50%, preferably greater than 55%, or even greater than 60%.

The surfactant is advantageously an anionic surfactant, a non-ionic surfactant, a cationic surfactant, or a mixture thereof. The molecular mass of the surfactant is between 150 g/mol and 10000 g/mol, advantageously between 250 g/mol and 1500 g/mol.

In the event the surfactant is an anionic surfactant, it is for example chosen from among an alkyl sulfate, an alkyl sulfonate, an alkyl aryl sulfonate, an alkaline alkyl phosphate, a dialkyl sulfosuccinate, a salt of saturated or unsaturated alkaline earth fatty acids. These surfactants advantageously have at least one hydrophobic hydrocarbon chain having more than 5, or even 10 carbons and at least one hydrophilic anionic group, a sulfonate or a carboxylate connected to one end of the hydrophobic chain.

In the case where the surfactant is a cationic surfactant, it is for example chosen from among a salt of alkylpyridinium or alkylammonium halide such as n-ethyl-dodecylammonium chloride or bromide, cetylammonium chloride or bromide (CTAB). These surfactants advantageously have at least one hydrophobic hydrocarbon chain having more than 5, or even 10 carbons and at least one hydrophilic cationic group, such as a quaternary ammonium cation.

In the event the surfactant is a non-ionic surfactant, it is for example chosen from among polyoxyethylenated and/or polyoxypropylenated derivatives of fatty alcohols, fatty acids, or alkylphenols, arylphenols, or among alkyl glucosides, polysorbates, cocamides.

The mass content in surfactant in the casing is greater than 0.001% and is advantageously greater than 0.1%.

In this example, the casing 14 is made up exclusively of polyelectrolyte, surfactant, and water. The sum of the mass content levels in polyelectrolytes, surfactants and water is then equal to 100%.

The method for manufacturing the capsules 10 according to the invention is implemented in a manufacturing device 30 according to the invention, shown in FIG. 1.

The manufacturing device 30 comprises a double casing 32 for co-extruding a series of drops intended to form capsules 10, a means 34 for bringing a first solution 36 intended to form the liquid core 12 into the double casing 32, and a means 38 for bringing a second solution 40 intended to form the gelled casing 14 into the double casing 32.

The device 30 also comprises a gelling bath 41A arranged under the double casing 32 and a rinse and storage bath 41B.

In a known manner, the double casing 32 comprises an inner tube 42 delimiting a central chamber 44 for circulation of the first solution 36, and an outer tube 46 delimiting, with the inner tube 42, an annular chamber 48 for circulation of the second solution 40.

The inner tube 42 and the outer tube 46 extend coaxially along a vertical axis A-A'. They emerge downwards through an opening 50 for forming each drop.

The inner tube 42 advantageously has a diameter larger than 0.5 mm and substantially between 0.6 mm and 2 mm.

The outer tube 46 has a diameter larger than the inner tube 42 by at least 0.2 mm, advantageously at least 0.4 mm. The maximum diameter of the outer tube 46 is smaller than 5 mm.

Each tube 42, 46 has a transverse section converging downwardly near the opening 50.

The means 34 for bringing in the first solution 36 comprises a first pump 52 for distributing the first solution 36, hydraulically connected downstream to the central chamber 44 by a first conveying pipe 54.

The first pump 52 is advantageously a syringe pump able to command a given injection flow rate Q1 of the first solution 36 into the central chamber between 1 ml/h and 120 ml/h, preferably in the range between 50 ml/h and 80 ml/h.

The means 38 for bringing in the second solution 40 comprises a second pump 56 for distributing the second solution 40, connected downstream to the annular chamber 48 via a second conveying pipe 58.

The second pump 56 is advantageously a syringe pump able to command the injection flow rate Q2 of the second solution 40 into the annular chamber 48 whether this flow rate Q2 is between 0.005 time and 0.2 time the flow rate Q1 commanded by the first pump 52. The first solution 36 is formed by the or each first pure liquid product, a solution of the or each first product in a liquid solvent, a dispersion such as an emulsion or a suspension of the or each first product in a liquid as described above.

The second solution contains the liquid polyelectrolyte suitable for gelling intended to form the liquid casing 12, the water and, according to the invention, at least one surfactant making it possible to produce the capsules 10.

The polyelectrolyte was described in detail above and will not be described again. It is completely dissolved in the water forming the second solution.

The mass content of the polyelectrolyte in the second solution is greater than the mass content of the polyelectrolyte in the casing 14. In the second solution, this mass content is greater than 0.1% and is for example between 0.1% and 5% by weight of the second solution.

The or each surfactant was described above. The mass content of surfactant is between 0.01% and 1% by mass of the total mass of the second solution.

If the composition of the liquid core 12 is primarily aqueous, the surfactant concentration in the second solution is advantageously between 0.01% and 0.5% by mass. If the composition of the liquid core 12 is primarily oily, the surfactant concentration is between 0.1% and 0.5% by mass.

Advantageously, the surfactant concentration by mass is about 0.03% for an aqueous liquid core 12 and about 0.15% for an oily liquid body 12.

The second solution is prepared by dissolving the surfactant in the quantity of water necessary to form the second solution. Then, the polyelectrolyte is added to the surfactant solution in the water and is mixed using a magnetic bar for a given time, for example at least 24 hours, at ambient temperature.

The bath 41A contains a gelling solution 70. This solution 70 is for example an aqueous solution of a reagent of type $X_nI_m$ where X is advantageously a halide ion such as a chloride ion, a bromide ion, an iodide ion, or a fluoride ion, and I is advantageously a multivalent cation of an alkaline earth such as calcium, magnesium, or barium, and n and m are greater than or equal to 1.

The multivalent ions present in the gelling solution 70 thus formed are able to react with the polyelectrolyte to form bonds between the different polyelectrolyte chains present in the second solution, when the second solution comes into contact with the gelling solution 70.

In the case where the polyelectrolyte is a sodium alginate (NaAlg), and where the reagent is calcium chloride, the reaction that occurs is the following:

$$2NaAlg + CaCl_2 \rightarrow Ca(Alg)_2 \downarrow 2NaCl$$

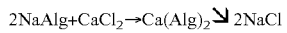

The concentration of reagent in the gelling solution is advantageously between 5% and 20% by mass.

The bath 41A is arranged below and away from the opening 50, so that the drops formed by co-extrusion in the double casing 32 fall spontaneously by gravity through a volume of air in the gelling solution 70 where they are submerged.

The rinse bath 41B comprises a rinse and storage solution formed essentially by water.

A first method of forming capsules 10 according to the invention will now be described.

This method comprises a step for forming a drop 78 comprising a core 80 of a first solution and an outer film 82 of second solution by co-extrusion in the device 32. The method then comprises a step for soaking the drop 78 in the gelling bath 41A, followed by a rinsing/storage step in the rinse bath 41B.

Initially, the first solution 36 and the second solution 40 are prepared as described above with the polyelectrolyte and surfactant weight loads described above.

They are then respectively introduced into the pumps 52, 56, which are connected to the double casing 32 by the first pipe 54 and the second pipe 58, respectively.

The first pump 52 is then activated to convey a continuous flow of first solution 36 through the central chamber 44 with a calibrated flow rate Q1 advantageously between 10 ml per hour and 80 ml per hour, as seen above.

The second pump 56 is activated to simultaneously convey a continuous flow of second solution 40 through the annular space 48 at a flow rate Q2 for example commanded between 0.005 time and 0.2 time the flow rate Q1 of the first solution 36.

The relative and independent adjustment of the flow rates Q1 and Q2 makes it possible to control the thickness of the casing 14 independently of the outer diameter of the capsule 10.

By significantly reducing the flow rate Q2, it is also possible to obtain capsules 10 with a gelled casing 14 with a very small thickness, in particular less than 0.5% of the diameter of the capsule 10, owing to the presence of the surfactant in the second solution 40.

At the opening 50, a substantially spherical drop 78 gradually forms with a core 80 made up exclusively of first solution and a fine film 82 of second solution completely surrounding the outer surface of the core 80.

The core 80 is made up entirely of first solution 36. In the film 82, the polyelectrolyte is kept in its liquid state as in the second solution.

When the weight of the drop 78 is greater than its capillary action retaining force on the tubes of the second casing 32, the drop 78 detaches from the double casing 32 by gravity and falls into the gelling bath 41A.

The film 82 is then in contact with the gelling solution. In contact with the multivalent ions coming from the gelling reagent, the individual chains of polyelectrolytes present in the film 82 connect to each other to form a reticulated array that traps the water and at least partially traps the surfactant contained in the second solution.

A gelled casing 14 able to retain the liquid core 12 of first liquid solution is thus formed. This casing 14 has its own mechanical strength, i.e. it is capable of completely surrounding the liquid core 12 and retaining the liquid present in this core 12 to prevent it from spreading through the casing 14, in particular when the capsule 10 is arranged in a gas such as ambient air.

Very surprisingly, the presence of surfactant in the second solution significantly favors the formation of capsules 10, in particular preventing the film 82 from undergoing a damaging phase separation during its soaking in the gelling solution 70.

Then, another drop 78 forms at the lower end 50 of the double casing 32 and the steps of the method are then identical to those described before.

Once the capsules 10 are formed, they are transferred into the rinse solution 72 for storage. The capsules 10 thus formed therefore sealably store various compounds such as biologically active products, proteins, cosmetic products, or comestible products for human or animal consumption.

During the use of the capsules 10, the casing 12 is broken by shearing, or mechanical crushing, or chelation of the multivalent ions, using a suitable salt such as EDTA, in the event calcium ions are used to form the gel for the casing. This rupture makes it possible to recover the first product present in the core 12.

In one alternative use, the recovered capsules are submerged in a liquid to swell, then explode by controlling the osmotic pressure through the gelled casing.

The opening of the casing 14 then frees the liquid core 12. This applies in particular to capsules 10 containing a syrup.

To inflate the capsule 10, a polymer such as a polyethylene glycol with a molecular mass greater than 5,000 g/mol is added to the core.

Alternatively, the osmotic pressure is controlled to retract the capsules 10 and decrease their diameter. It is then possible to dry or freeze dry the capsules 10.

In one alternative, magnetic particles can be added in the first solution 36 and/or the second solution 40, to modify the manipulation of the eggs.

Also alternatively, straws are added in the first solution 36 and/or the second solution 40 to create an optical effect on the capsules 10.

Figure 3:
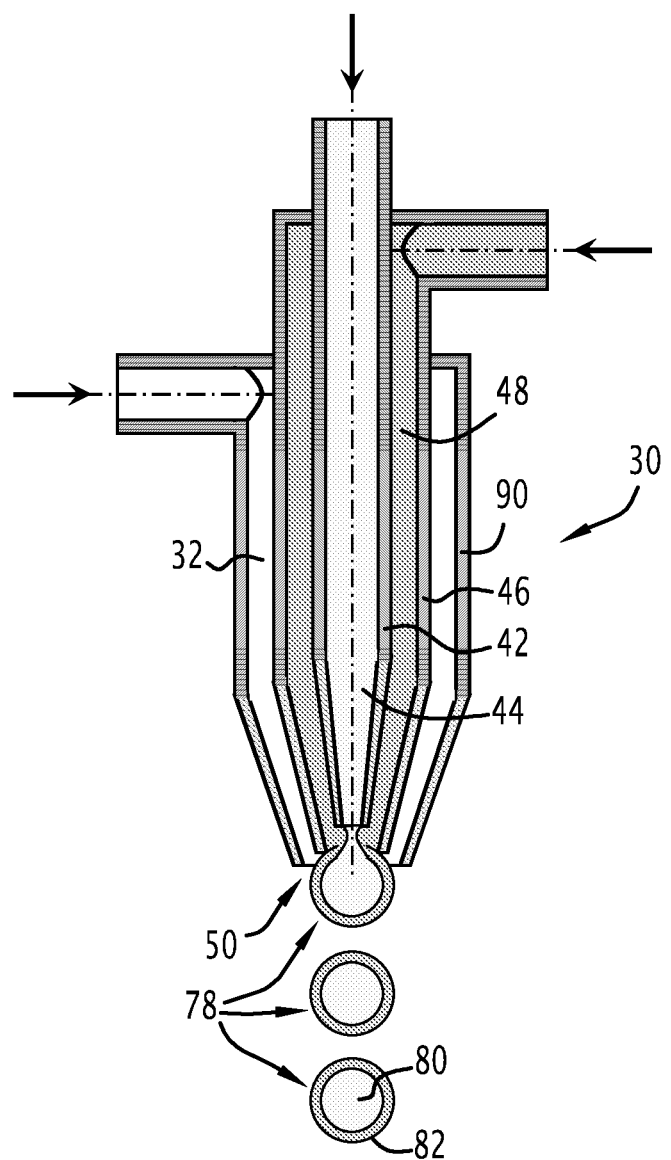
FIG. 3 is a view similar to FIG. 1 of a detail of a second device for manufacturing capsules according to the invention.

One alternative of the production device 30 for capsules 10 is illustrated by FIG. 3. Unlike the device shown in FIG. 1, this device comprises, around the double casing 32, an outer gas injection casing 90 extending annularly around and away from the outer tube 46.

The outer casing 90 emerges axially around the opening 50. It is connected to a compressed gas source to create, around the drop 78 being formed, a flow of gas oriented downwards.

The flow rate of this gas flow can be adjusted to control the size of the drops 78 formed at the outlet of the double casing 32.

The capsule production method 10 using the device 30 according to FIG. 3 differs from the method implemented with the device 30 of FIG. 1 in that the size of the drops 78 can be adjusted by adjusting the gas flow.

Figure 4:
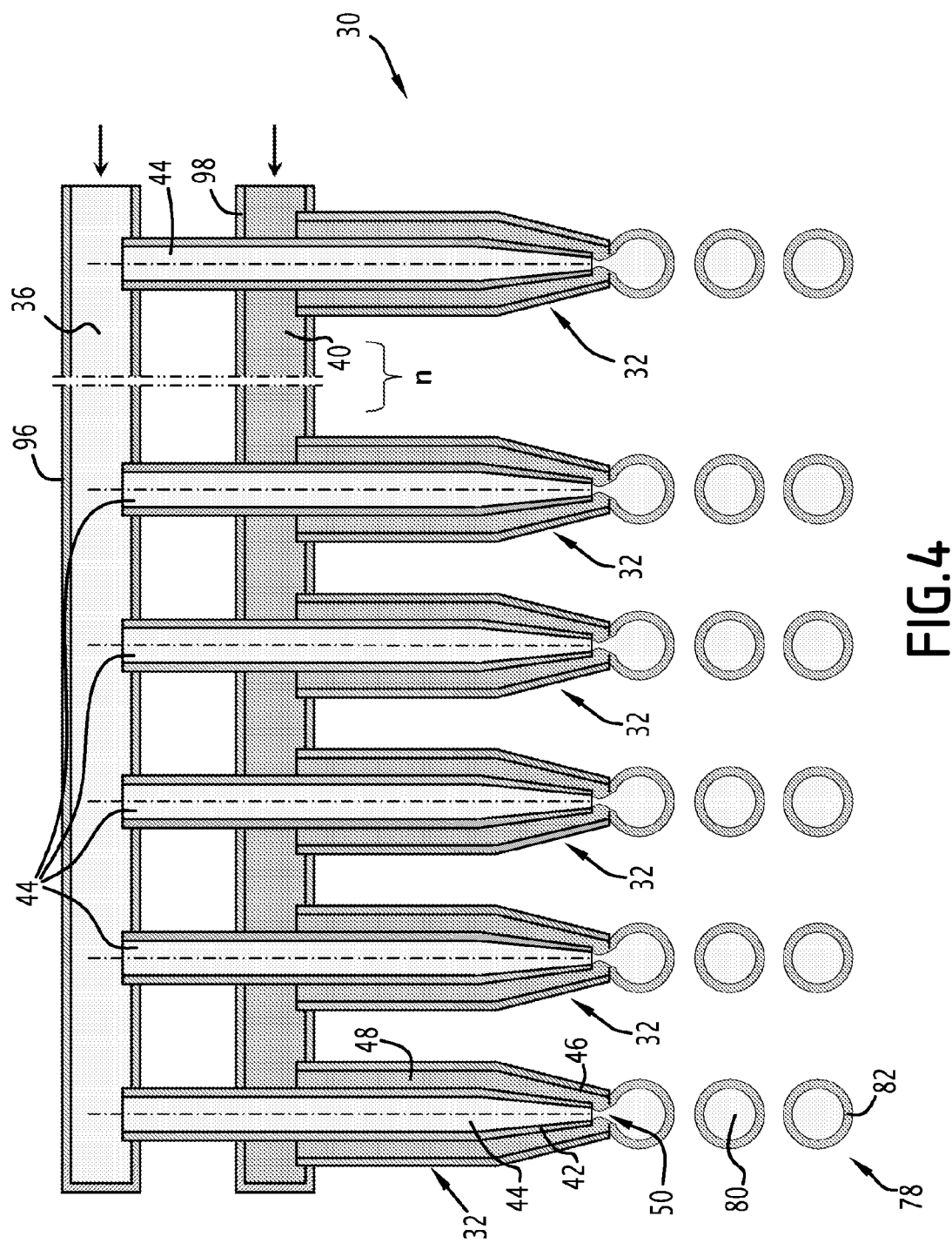
FIG. 4 is a cross-sectional view along a median vertical plane of a third device for manufacturing capsules according to the invention.

FIG. 4 illustrates a third device 30 for forming capsules that comprises a plurality of double casings 32 arranged in parallel next to each other. The intake means 34 for the first solution 36 comprises, at the end of the first pipe 54, a shared distributor 96 for the first solution, in which each central chamber 44 of the parallel double casings 32 emerges.

The intake means 38 of the second solution 40 comprises a shared distributor 98 of the second solution 40 emerging in each annular chamber 48 of the double casings 32 mounted parallel. In this way, this device 30 makes it possible to form a number of parallel drops equal to the number of double casings 32 mounted parallel, which increases the device's overall productivity.

In one alternative, in the case where the core 12 assumes the form of an emulsion, this emulsion can be made by co-extrusion within an additional tube placed in the inner tube 42 during production of the capsule 10.

It is thus possible to form cores 12 for example containing vinaigrette.

Examples of first solution and second solution compositions having been used to successfully form capsules 10 according to the invention are described in the table below, in which all of the percentages are weight percentages. The solvent of the second solution is water. PEG is a polyethylene glycol whereof the molar mass is also provided in the table.

SDS is sodium dodecyl sulfate (anionic surfactant) CTAB is Cetyl Trimethylammonium Bromide (cationic surfactant), Tween 20 is polyoxyethylene sorbitan monolaurate (non-ionic surfactant), and Tween 80 is polyoxyethylene sorbitan monooleate (non-ionic surfactant).

| First solution composition for the core | Second solution composition for the casing |
|---|---|
| | WITH SDS |
| Water milliQ | 2% sodium alginate, 0.03% SDS |
| Water + 0.5% PEG20000 g/mol | 1.5% sodium alginate, 0.03% SDS |
| Water + 0.5% PEG20000 g/mol | 2% sodium alginate, 0.03% SDS |
| Water + 0.5% PEG20000 g/mol | 3% sodium alginate, 0.03% SDS |
| Water + 1% PEG 20000 g/mol | 2% sodium alginate, 0.03% SDS |
| Water + 2% PEG 20000 g/mol | 2% sodium alginate, 0.03% SDS |
| Water + 4% PEG 20000 g/mol | 2% sodium alginate, 0.03% SDS |
| Water + 0.5% PEG 35000 g/mol | 2% sodium alginate, 0.03% SDS |
| Water + 15% PEG 35000 g/mol | 2% sodium alginate, 0.03% SDS |
| Water + 20% PEG 35000 g/mol | 2% sodium alginate, 0.03% SDS |
| Mango puree | 2% sodium alginate, 0.03% SDS |
| 80% mango puree + 20% syrup at 15% sugar | |
| Pear puree | 2% sodium alginate, 0.03% SDS |
| 80% pear puree + 20% syrup at 15% sugar | |
| Cocoa powder solution | 2% sodium alginate, 0.03% SDS |
| 10% cocoa powder + 90% syrup at 30% sugar | |
| Olive oil | 2% sodium alginate, 0.15% SDS |
| Olive oil + 2% basil mixed | 2% sodium alginate, 0.15% SDS |
| Soy oil | 2% sodium alginate, 0.15% SDS |
| Grape seed oil | 2% sodium alginate, 0.15% SDS |
| Grape seed oil | 0.5% sodium alginate, 0.15% SDS |
| Hexadecane | 2% sodium alginate, 0.15% SDS |
| | WITH CTAB |
| Water milliQ | 2% sodium alginate, 0.02% CTAB |
| Water milliQ | 2% sodium alginate, 0.03% CTAB |
| | WITH TWEEN |
| Water MilliQ | 2% sodium alginate, 50 mM Tween 20 |
| Water MilliQ | 2% sodium alginate, 53 mM Tween 80 |

One example of an operating mode for preparing capsules is the following:

Formation of the Second Solution:

Composition for Capsules with an Aqueous Core Using an Anionic Surfactant:

One prepares 20 g of sodium alginate, 1,000 g of water and 0.3 g of SDS. The SDS and the sodium alginate are then added into the solution. The solution is mixed for at least 24 hours to make sure the alginate is completely dissolved and the solution is homogenous.

Composition for Capsules with an Oily Core Using an Anionic Surfactant:

One prepares 20 g of sodium alginate, 1,000 g of water and 1.5 g of SDS. The SDS is dissolved in water and the sodium alginate is then added. The solution is mixed for at least 24 hours to make sure the alginate is completely dissolved and the solution is homogenous.

Composition for Capsules with an Aqueous Core Using a Cationic Surfactant:

One prepares 20 g of sodium alginate, 1,000 g of water and 0.36 g of CTAB. The CTAB is dissolved in the water and the sodium alginate is then added. The solution is mixed for at least 24 hours to make sure the alginate is completely dissolved and the solution is homogenous.

Composition for Capsules Having an Oily Core Using a Cationic Surfactant:

One prepares 20 g of sodium alginate, 1,000 g of water and 1.8 g of CTAB. The CTAB is dissolved in the water and the sodium alginate is then added. The solution is mixed for at least 24 hours to make sure the alginate is completely dissolved and the solution is homogenous.

Preparation of the First Solution

The solution of the core can be aqueous or oily. It can contain one or more phases.

Bath of Gelling Saline Solution

This bath can be prepared with a base of 200 g of calcium chloride dissolved in 1,000 g of water. Alternatively, it can be prepared with a base of 50 g of calcium lactate pentahydrate dissolved in 1,000 g of water.

In one alternative, the capsules 10 prepared using the inventive method do not have a detectable quantity of surfactant of the second solution.

The method of forming capsules 10 as described above makes it possible to obtain capsules of uniform size. This makes it possible to use them as dosage unit in the cosmetic, dermatological or parapharmaceutical fields.

In this way, it is possible to provide for a cosmetic treatment in which a number of capsules to be applied on the skin or ingested are assayed.

The number of capsules to be used, the application frequency or ingestion of these capsules and the length of the treatment can vary according to the characteristics of the person undergoing the treatment.

In this same technical field, the capsules 10 can be used with a core 12 that comprises a hydrating cream for the skin, various capillary treatments, lip gloss.

In this way, it is possible to explode a capsule 10 containing gloss between a user's lips, the gloss being distributed by rubbing the lips together.

In this type of application, straws can be added into the core 12 or into the casing 14 of the capsule to obtain optical effects such as brilliance, reflections, radiance.

The capsules 10 according to the invention can also be used in the agri-food field to obtain flavor beads.

In this way, the capsules formed containing a food product can be used for example to form a synthetic caviar.

In the agri-food industry, the capsules 10 can also be used in sweetening pellets by being added to beverages. The capsules that for example contain a polymer or another product, making it possible to swell or deflate them by osmotic pressure, allow a product contained in the core 12 to spread in the beverage or in a liquid dish. In this way, through swelling or deflation of the capsule, it is possible to make it explode more freely to release the product contained in the core 12.

The capsules 10 according to the invention can also be used in the biotechnology field as a cell growth reservoir, to perform illness detection biological tests.

It is thus possible to use capsules 10 according to the invention to facilitate screening under different environmental conditions.

Moreover, the addition of magnetic particles in the casing 14 makes it possible to immobilize cells in the core 12 of the capsule 12 to form a bioreactor.

The invention claimed is:

1. A method for manufacturing a capsule series (10), each capsule (10) comprising a liquid core (12) containing at least one first product and a gelled casing (14) completely encapsulating the core (12), the method comprising the following steps:

separately conveying, in a double casing (32), a first liquid solution (36) containing the first product and a second liquid solution (40) containing a liquid polyelectrolyte able to gel;

forming, at the outlet (50) of the double casing (32), a series of drops (78), each drop (78) comprising a central core (80) formed from the first solution (36) and a peripheral film (82) formed from the second solution and completely covering the central core (80);

immersing each drop (78) in a gelling solution (70) containing a reagent able to react with the polyelectrolyte of the film (82) to make it go from a liquid state to a gelled state and form the gelled casing (14), the central core (80) forming the liquid core (12), wherein the drops (78) formed by co-extrusion in the double casing (32) fall by gravity through a volume of air into the gelling solution (70);

recovering the capsules (10) formed;

wherein the second solution (40) contains at least one surfactant before the former contacts the first solution (36); and wherein the flow rate of the second solution (40) is comprised between 0.005 times and 0.2 times the flow rate of the first solution (36) at the outlet of the double casing (32).

2. The method according to claim 1, wherein the or each surfactant is chosen among an anionic surfactant, a cationic surfactant, a non-ionic surfactant, or mixtures thereof.

3. The method according to claim 2, wherein the surfactant is chosen from among an alkyl sulfate, an alkyl sulfonate, an alkyl aryl sulfonate, an alkaline alkyl phosphate, a dialkyl sulfosuccinate, a salt of saturated or unsaturated alkaline earth fatty acids, a salt of alkylpyridinium or alkylammonium halide such as n-ethyl-dodecylammonium chloride or bromide, cetylammonium chloride or bromide, polyoxyethylenated and/or polyoxypropylenated derivatives of fatty alcohols, fatty acids, or alkylphenols, or among arylphenols, alkyl glucosides, polysorbates, cocamides, or mixtures thereof.

4. The method according to claim 3, wherein the total weight percentage of surfactant in the second solution (40) is greater than 0.01%.

5. The method according to claim 1, wherein the or each polyelectrolyte is a polyelectrolyte reactive to multivalent ions.

6. The method according to claim 5, wherein the ion-reactive polyelectrolyte is an alginate alkaline.

7. The method according to claim 5, wherein the weight percentage of polyelectrolyte in the second solution (40) is less than 5%.

8. The method according to claim 1, wherein the first solution comprises (36) at least one of a biologically active product, a cosmetic product, or a comestible product suitable for consumption.

9. A capsule series (10), each capsule (10) comprising a liquid core (12) containing at least one first product, and a gelled casing (14) completely encapsulating the liquid core (12) at the periphery thereof, the gelled casing (14) being able to retain the liquid core (12) when the capsule (10) is submerged in a gas, the gelled casing (14) comprising at least one gelled polyelectrolyte;

wherein the gelled casing (14) also comprises at least one surfactant; and wherein the gelled casing (14) has a thickness between 0.1% and 10% of the diameter of the capsule (10).

10. The method according to claim 6, wherein the weight percentage of polyelectrolyte in the second solution (40) is less than 5%.

11. The method according to claim 1, wherein the ratio of the flow rate of the first solution (36) to the flow rate of the second solution (40) at the outlet of the double casing (32) is between 10 and 200.

12. The method according to claim 1, wherein the gelled casing (14) has a thickness between 0.1% and 2% of the diameter of the capsule (10).

13. The method according to claim 3, wherein the total weight percentage of surfactant in the second solution (40) is between 0.01% and 0.5%.

14. The method according to claim 1, wherein the or each polyelectrolyte is a polysaccharide reactive to multivalent ions.

15. The method according to claim 14, wherein the polysaccharide reactive to multivalent ions is chosen from among an alginate alkaline, a gellan, or a pectin.

16. The method according to claim 5, wherein that the ion-reactive polyelectrolyte is an alginate alkaline advantageously having an α-L-guluronate block content greater than 55%.

17. The method according to claim 5, wherein the weight percentage of polyelectrolyte in the second solution (40) is between 0.5 and 3%.

18. The capsule series (10) according to claim 9, wherein each capsule (10) has a gelled casing (14) with a thickness between 0.1% and 2% of the diameter of the capsule (10).

19. The method according to claim 6, wherein the weight percentage of polyelectrolyte in the second solution (40) is between 0.5 and 3%.

* * * * *

UNITED STATES PATENT AND TRADEMARK OFFICE
CERTIFICATE OF CORRECTION

| | | |
|---|---|---|
| PATENT NO. | : 9,277,759 B2 | Page 1 of 1 |
| APPLICATION NO. | : 13/131971 | |
| DATED | : March 8, 2016 | |
| INVENTOR(S) | : Jerome Bibette et al. | |

It is certified that error appears in the above-identified patent and that said Letters Patent is hereby corrected as shown below:

On the title page, please amend Item (73) to read as follows:

-- (73) Assignee: CAPSUM, Marseille (FR) --

Signed and Sealed this
Third Day of May, 2016

Michelle K. Lee
*Director of the United States Patent and Trademark Office*